United States Patent
Trebbia et al.

(10) Patent No.: US 7,391,517 B2
(45) Date of Patent: Jun. 24, 2008

(54) METHOD AND DEVICE FOR MEASURING THE ABSORPTION OR LIGHT DIFFUSION OF BIOLOGICAL ELEMENTS

(75) Inventors: Jean-Baptiste Trebbia, Gif sur Yvette (FR); Patrick Chaton, Theys (FR); Stephane Getin, Grenoble (FR); Philippe Grosse, Sassenage (FR)

(73) Assignee: Commissariat a l'Energie Atomique, Paris (FR)

( * ) Notice: Subject to any disclaimer, the term of this patent is extended or adjusted under 35 U.S.C. 154(b) by 376 days.

(21) Appl. No.: 11/019,266

(22) Filed: Dec. 23, 2004

(65) Prior Publication Data

US 2005/0158868 A1 Jul. 21, 2005

(30) Foreign Application Priority Data

Dec. 26, 2003 (FR) .................................. 03 51212

(51) Int. Cl.
*G01N 21/00* (2006.01)
(52) U.S. Cl. ......................................... 356/432; 356/440
(58) Field of Classification Search ......... 356/432–440, 356/454, 484; 250/343; 600/532
See application file for complete search history.

(56) References Cited

U.S. PATENT DOCUMENTS

| | | | | |
|---|---|---|---|---|
| 5,237,584 A | * | 8/1993 | Shannon et al. ............... | 372/93 |
| 5,696,786 A | * | 12/1997 | Durkin et al. ................. | 372/75 |
| 5,903,358 A | * | 5/1999 | Zare et al. .................... | 356/437 |
| 5,946,330 A | * | 8/1999 | Ozygus et al. ................ | 372/19 |
| 6,392,753 B1 | * | 5/2002 | Logunov ..................... | 356/519 |
| 6,452,680 B1 | | 9/2002 | Paldus et al. | |
| 6,532,072 B1 | * | 3/2003 | Largent ...................... | 356/440 |
| 7,012,696 B2 | * | 3/2006 | Orr et al. ..................... | 356/454 |
| 7,101,340 B1 | * | 9/2006 | Braun ........................ | 600/532 |
| 2003/0007715 A1 | * | 1/2003 | Loock et al. .................. | 385/12 |
| 2006/0087655 A1 | * | 4/2006 | Augustine et al. ........... | 356/437 |

OTHER PUBLICATIONS

Steven S. Brown, et al., "Simultaneous in situ detection of atmospheric $NO_3$ and $N_2O_5$ via cavity ring-down spectroscopy", Review of Scientific Instruments, American Institute of Physics, XP-001132680, vol. 73, No. 9, Sep. 2002, pp. 3291-3301.
D. Kleine, et al., "Cavity ring-down spectroscopy of molecularly thin iodine layers", Appl. Phys. B 72, Lasers and Optics, XP-002276176, 2001, pp. 249-252.
A.C. Boccara, et al., Thermo-optical spectroscopy: Detection by the "mirage effect", Appl. Phys. Lett. 36(2), Jan. 15, 1980, pp. 130-132.
Jiri Homola, et al., "Surface plasmon resonance sensors: review", Sensors and Acuators B 54, 1999, pp. 3-15.

* cited by examiner

*Primary Examiner*—Hao Q Pham
(74) *Attorney, Agent, or Firm*—Oblon, Spivak, McClelland, Maier & Neustadt, P.C.

(57) ABSTRACT

A method and a device, using a system of plural cavity resonators, enabling to measure the light absorption or diffusion of biological samples. A measurement of low absorption or diffusion can be achieved and for example be applied for measuring the hybridization of DNA strands.

34 Claims, 7 Drawing Sheets

METHOD AND DEVICE FOR MEASURING THE ABSORPTION OR LIGHT DIFFUSION OF BIOLOGICAL ELEMENTS

BACKGROUND OF THE INVENTION

1. Field of the Invention

The present invention relates to an improved device enabling to measure the absorption and/or light diffusion of objects, as well as a method for measuring the absorption and/or light diffusion of biological elements.

2. Discussion of the Background

To measure the light absorption of biological elements, a well-known method is the photo-thermal deflection measurement. This method is presented in the document [1] listed at the end of the present description.

It consists of irradiating an object the absorption of which is to be measured using a "pump" beam. Part of the energy of the "pump" beam is then absorbed by the object and leads to a graded index in the surrounding environment(s). Another light beam, known as a "pumping" beam crossing this graded index then undergoes a deviation. Measuring the deviation of a "probe" beam can enable to quantify the graded index. This measurement then makes it possible to deduce the light absorption of the object.

This method is, however, limited. It may not be sufficiently precise for some applications that require a high degree of sensitivity of detection such as for example the measurement of the hybridization of DNA strands.

Another method, known as "resonance by surface plasmon", can be used to measure the light absorption of biological samples. This method is presented in document [2] listed at the end of the present description.

This "resonance by surface plasmon" method has the particular drawback of requiring adjustments which have to be renewed for each biological sample measured.

For some applications requiring the measurement of a large number of samples, as for example the measurement of DNA strands hybridization on a biochip, this method can turn out to be very long to implement.

The problem consists in being able to carry out detailed measurements of samples of biological elements more quickly than the methods under the previous technology.

SUMMARY OF THE INVENTION

The present invention proposes a method to measure biological samples light absorption or diffusion comprising the following steps of:
  a) Placing at least one target sample in at least one cavity resonator or optical cavity or in at least one cavity resonator or optical cavity of a multi-cavity system.
  b) Emitting at least one light impulse in the cavity.
  c) Measuring at least one light response signal from the cavity in response to the light impulse, the measurement of the light impulse enabling to determine the light absorption of the sample.

By biological sample is meant biological elements such as for example animal or vegetable cells, micro-organisms, bacteria, macro-molecules such as DNA or RNA.

The method according to the invention makes it possible to obtain measurements with higher sensitivity than with methods requiring to expose biological samples to be measured under a continuous beam.

The cavity can be formed for example by mirrors arranged opposite to each other. As for the light impulse(s) emitted in the cavity, they can come from a pulsed laser for example or a matrix of pulsed lasers. The response signal(s) coming from the cavity can be measured using a device with for example one or more photo-detectors, for example in the form of photodiodes or phototransistors. For example, a measurement of the response signal(s) decrease can enable to determine the absorption of the samples.

According to a variant of the invention, the cavity can be replaced by a multi-cavity system. This variant can enable to rapidly measure several samples.

Such a multi-cavity system can be formed for example by at least one first matrix of concave mirrors associated with a plane mirror or a second matrix of concave mirrors. The mirrors of the first matrix and/or the second matrix can be integrated to one support.

To measure several samples, the invention provides a variant method comprising the following steps of:
  a) Placing at least two target samples among the biological samples, each in a target cavity of the multi-cavity system,
  b) Emitting at least one light impulse in each of the said target cavities.
  c) Measuring at least two light response signals from target cavities in response to the light impulses, the measurements of the light signals enabling the light absorption of at least two samples to be determined.

This variant can enable to measure several samples in parallel, so as to obtain an <<image>> of the light absorption of a group of several samples.

According to a variant of the method the impulses can be emitted simultaneously at step b), using for example several pulsed lasers or a matrix of pulsed lasers.

At step c), the response signals can then be measured simultaneously or consecutively, for example using several detectors or a matrix of detectors, for example a matrix of photodiodes.

According to a variant of the device the emitting source of light impulses, a pulsed laser for example, can be associated to a device or means enabling light rays to be deflected.

Light impulses emitted in a cavity or a system of several cavities can then be sent to any sample of a group of samples without having to shift the source emitting the impulses.

The method according to the invention may enable to measure one or more very small biological samples. The samples can be for example arranged on a biochip placed inside the cavity of the multi-cavity system.

A system of several micro-cavities, for instance, arranged according to a matrix can also be set up to measure small samples. This system may be used for example to measure DNA or RNA samples grafted on biochip blocks. Such a system of micro-cavities can be formed for example, by using a thin coating method.

The cavity or multi-cavity system is formed of first reflectors means or a first reflector device and second reflector means or a second reflector device. In a variant of the method according to the invention, the biological samples, for example DNA or RNA, can be grafted or integrated or coupled to the first or second reflector means prior to step a). With grafted samples for example it is possible to measure the calibration on the reflectors prior to the sample grafting step.

This variant method enables to avoid using a support for samples. Measurement where only the absorption or light diffusion of samples is taken into account can then be carried out.

The invention also relates to a device for measuring the light absorption of objects including: first and second light ray reflectors, first and second reflectors being capable of forming a system of several resonant cavities.

In order to form a system of several cavities, first and/or second reflectors can include at least two mirrors or a matrix of mirrors. This minimum of two mirrors or the mirrors of the matrix of mirrors can be integrated to a single support.

According to a variant of this system of several cavities, the first reflectors can include a first matrix of concave mirrors, the second reflectors can then include a plane mirror or a second matrix of concave mirrors.

A device emitting light impulses in the cavities of the system can also be provided.

This emitting device can include for example one or more pulsed lasers or a matrix of pulsed lasers. The device according to the invention can possibly also include a coupling device or means to couple the emitting device and at least one cavity from the multi-cavity system. The coupling means can include for example one or more waveguides or at least one lens or at least one matrix of lens.

According to a variant of the device of the invention, a deflection device or means of deflecting light rays can be associated to the light impulse emitting device to, for example, direct impulses to any cavity of the multi-cavity system.

To measure signals coming from one or more cavities of the multi-cavity system the device according to the invention can also include a detection device including at least one photo-detector selected according to the wavelength of the signals for example, a photodiode or phototransistor or a matrix of photodiodes or a matrix of phototransistors.

The device according to the invention can include another coupling device or other means coming from the cavity or multi-cavity system to couple the detection device and at least one cavity of the system of several cavities. These other coupling devices can for example include one or more waveguides, or at least one lens or a matrix of lenses.

Means to focus the light rays from one or more cavities of the system of several cavities on the detection device can be provided.

Objects or elements measured using the device according to the invention can be biological samples, for example, DNA or RNA or cells.

The invention also relates to a device including a support with samples placed between the first and second reflectors, forming a cavity or a system of several cavities. It also relates to a device in which the samples are samples of biological elements grafted or integrated to the first or second reflectors of a cavity or a system of multi-cavities.

BRIEF DESCRIPTION OF THE DRAWINGS

The present invention will be better understood on reading a description of examples of implementation given purely for informative purpose and that are in no way restrictive, making reference to the drawing appended on which:

FIG. 1 illustrates an example of implementing a method according to the invention, FIGS. 2A, 2B respectively illustrate curves of a light impulse emitted at the entrance of an optical cavity resonator and signal coming out of the cavity in response to the impulse, FIG. 6 illustrates an example of a variable transmission mask, Parts that are identical, similar or equivalent to the different figures have the same numerical references so as to facilitate passage from one figure to another.

In order to make the figures more legible the different parts represented on the figures are not necessarily represented according to a uniform scale.

DETAILED PRESENTATION OF PARTICULAR EMBODIMENTS

An example of a device set up according to the present invention will now be described in connection with FIG. 1. This device includes reflector means 108, for instance the first of one or more plane and/or concave mirrors and second reflector means 109 reflectors, for instance formed by one or more plane and/or concave mirrors.

These first and second reflectors 108 and 109 are parallel and arranged opposite to each other. They form at least one Fabry-Pérot optical cavity resonator surrounding the samples 105. This cavity can be between a few centimetres and a few meters long, for example 10 cm.

A device makes it possible to send light impulses 116 in the cavity. It includes an emitting source 115, a pulsed laser for example, making it possible to send short light impulses for a period of between 100 picoseconds and several dozen nanoseconds or 100 nanoseconds for example, at a frequency of between a few kHz and a few hundred kHz and in a range of wavelengths from ultraviolet to infrared.

Figure 2A:
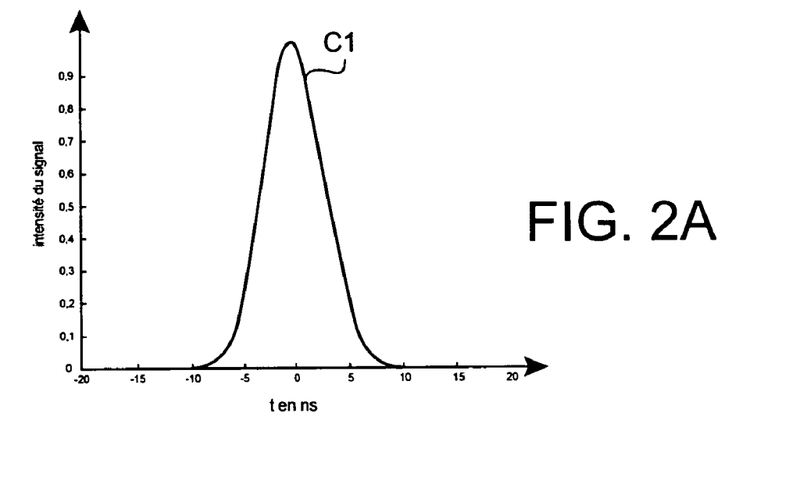

The curve $C_1$ on FIG. 2A illustrates an example of a signal sent by the emitting source 115 to the entrance of the cavity.

When a light impulse is emitted at the cavity entrance, it propagates inside the latter, then it reflects a number of times in turns on second reflectors 109 and then on first reflectors 108. A weak part of the energy of the impulse escapes from the cavity after each round trip.

By providing a detection device 120 at the cavity exit, it is possible to collect the light energy transmitted coming from the cavity. For a light signal emitted at the entrance of the cavity in the form of an impulse, a response signal exiting from the cavity in the form of a series of impulses is obtained using the detection device 120.

A support 100 comprising objects whose absorption and/or the light diffusion is to be measured, is placed in the cavity. These objects are for example samples 105 of biological elements like animal or vegetable cells, micro-organisms, macro-molecules like DNA and RNA.

The response signal coming out of the cavity thus has an envelope showing the losses caused by the cavity and by the support 100 with samples 105. This envelope generally decreases exponentially with time.

Figure 2B:
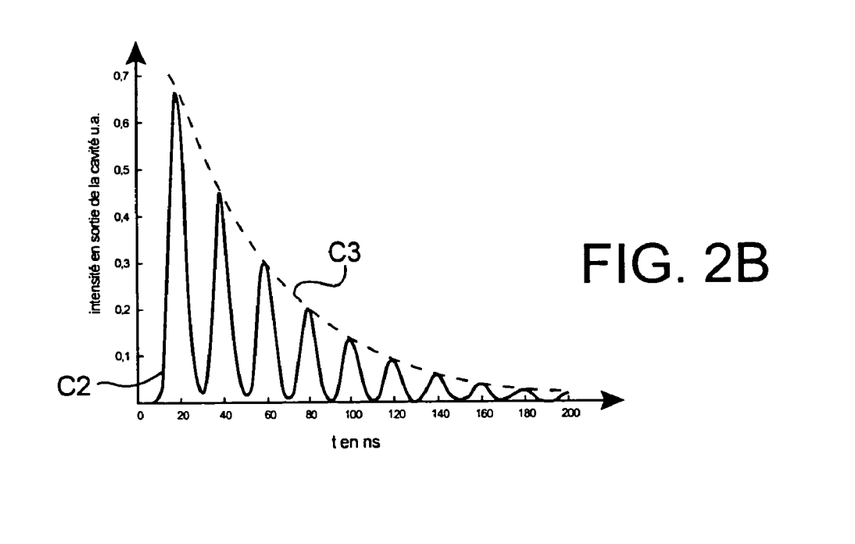

An example of a signal coming out of the cavity and in response to that illustrated by curve $C_1$ on FIG. 2A is represented by curve $C_2$ of FIG. 2B. It has the shape of a series of pulses of weaker and weaker amplitudes. The envelope of this response signal is modelled by the curve $C_3$ in dotted lines, taking the form of an exponential decrease.

Following the emitting of a light impulse at the entrance of a cavity, measuring the fall time of the response signal coming out of the cavity enable to know the losses caused by this cavity. The presence of an object like the support 100 inside the cavity engenders additional losses of energy compared to an empty cavity and modifies the value of the fall time.

Likewise the presence of samples 105 of biological elements on the support 100 inside the cavity engenders additional energy losses compared to a cavity with this same support 100 and without samples.

To measure the absorption of samples of biological elements, one can first measure the fall time of a response signal coming from the cavity when this cavity includes the support 100 without the samples 105. This measurement is then compared with another measurement of the fall time of a response signal coming from the cavity when this cavity includes the support 100 with samples in addition.

To make these measurements the impulses sent into the cavity have a temporal width, particularly according to the length of the cavity. This temporal width will preferably not exceed a threshold value so as to prevent spatial overlap of two successive impulses coming from the cavity. For example for a 10 cm long cavity, the temporal width of light impulses sent will preferably be less than 666 picoseconds. According to another example, for a 1 meter length cavity the temporal width of the light impulses sent will preferably be less than 6.6 nanoseconds.

As for the instantaneous power of the impulses, these impulses can for example be between a dozen kilowatts and several hundred kilowatts, for example of the order of 166 kW.

The fall time of a response signal coming from the cavity like the one shown in FIG. 2B, depends in particular on the length of the cavity and on the reflectivity of reflector means 108 and 109. For example for a 10 cm long cavity and reflectors with a reflectivity ratio of 99.8%, this fall time can be of the order of a hundred nanoseconds, equal to 166 ns for instance. Thus the length of the cavity is chosen so that the fall time of the output signal remains measurable.

When the response signal coming from the cavity is received by the detection device, this signal may have a decreasing amplitude in a maximum order of one or more/ with a maximum of the order of one or more hundred milliwatts, or 6.66 mW for reflector means forming the cavity, having each a reflectivity of 99.8% and for an emitted impulse power at the entrance of the cavity of the order of 166 kW.

Attenuation of the detection device can for example be of the order of 20 dB. The latter can include one or more detectors for example one or more photodiodes, enabling to acquire light response signals coming out from the cavity and to transform these light response signals into electrical signals. The photon-current conversion of these detectors can be of the order of a few hundred milliamperes by watts, for example of the order of 0.3 A/W.

The measured response signal coming out from the cavity, converted into a current by these photodiodes and attenuated, can have a maximum amplitude of one or more hundred microamperes. This amplitude can for example be 222 microamperes for a signal at the entrance of the detection device of the order of 6.66 mW and an attenuation of the order of 20 dB.

Figure 1:
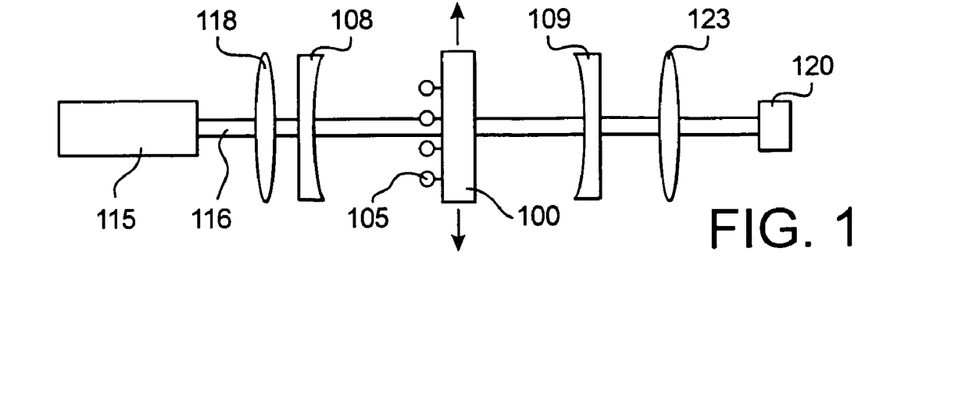

The device previously described and illustrated in FIG. 1 can also be equipped with optical coupling means 118, for example in the form of one or more lenses situated between the emitting source 115 and the cavity. These couplings 118 can enable to adjust the light impulses coming from the source 115 compared to the optical axis of the cavity.

On the other hand, according to the characteristics of source 115, according to the diameter and the divergence of the laser beam for example, the coupling means 118 can enable to couple the source 115 with the normal mode of the cavity.

Other coupling means 123 can also be provided for to collect the light rays coming from the cavity 110 and enable to focus this ray on the detection device 120. These other coupling means 123 can for example take the form of one or more lenses located between the cavity and the detector device 120.

According to a variant of the method, the support 100 can be moved relatively to the reflector means 108 and 109, after each measurement. This can enable each of the samples 105 to be placed in turn in the cavity resonator without necessarily having to move the coupling means 118 or the emitting source 115 of light impulses. Means to move the support 100, automated for example, can be provided for. These shifting means of movement can include for example a step-by-step motor as well as a translation plate.

According to a variant of the invention, a system of several cavity resonators that will be called a "multi-cavity system" can be used in place of a single cavity. This system can enable rapid measurement of the light absorption of several biological samples, particularly without necessarily having to move the support of the samples to be measured.

Figure 3A:
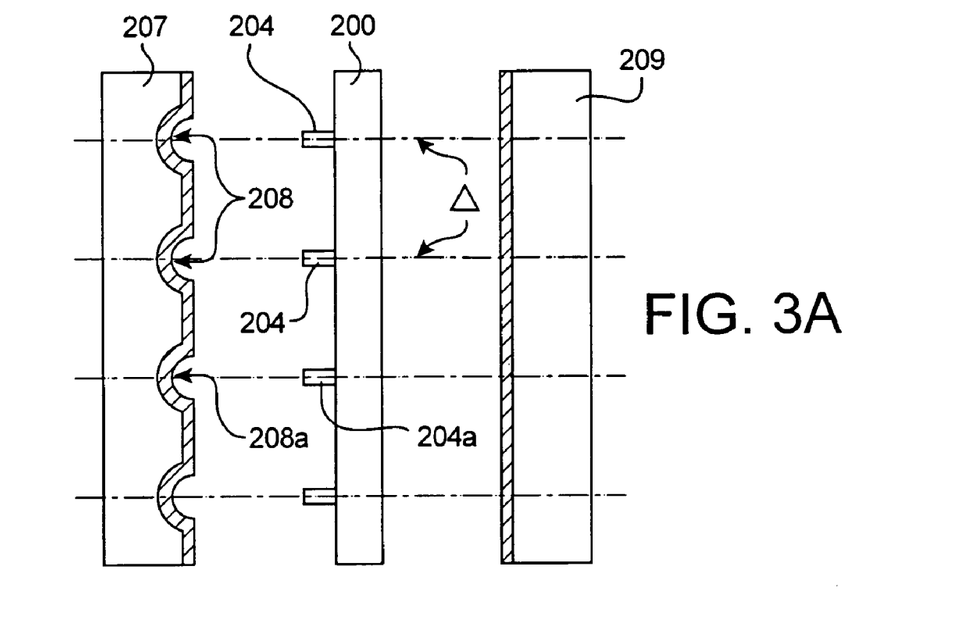
FIGS. 3A, 3B, 3C, 3D, 3E illustrate examples of devices including a multi-cavity system according to the invention.

FIG. 3A illustrates an example of a device comprising a multi-cavity system.

This device includes first of all a matrix 207 of concave mirrors 208 and a plane mirror 209, the matrix 207 and the plane mirror 209 being opposite one to another and parallel. Each mirror of the matrix 207 associated to a portion of the plane mirror 209 forms a cavity resonator with an optical angle A (represented by dotted lines) on which samples can be centred.

A biochip 200 with biological samples whose light absorption is to be measured is placed in the system. Biological samples are for example DNA or RNA strands grafted on to the blocks 204.

To measure the absorption of a particular sample placed on a particular block 204a included in a particular cavity of the multi-cavity system, one can preserve the principle of the method described above. A series of light impulses is emitted for example using a laser beam on the rear face of a particular concave mirror 208a of the matrix 207.

A response signal of these impulses coming from this special cavity is then measured. To measure another sample the laser beam can then be moved to the entrance of another cavity including this other sample.

Mirrors 208 of the matrix can have a diameter comprised for example between 100 micrometers and a few/some millimetres for example of the order of 1 mm or 2 mm.

The size or diameter of the mirrors 208 of the matrix 207 will preferably have a value that is higher than the diameter of the laser beam sent to the entrance of the multi-cavity system. In the opposite case undesirable diffraction phenomena on mirrors can appear. This can also lead to losses likely to distort the measurements made.

For these losses to be lower than 100 ppm, the mirrors will preferably have a radius at least 2.74 times greater than the diameter of the beam on the mirror.

For these losses to be less than 10 ppm, the mirrors will preferably have a radius at least 3.19 times greater than that of the beam on the mirror.

For these losses to be less than 1 ppm, the mirrors will preferably have a radius at least 3.45 times less than the diameter of the beam on the mirror.

The size as well as the curve radius of the mirrors 208 of the matrix 207 can also be adapted to the size of the samples.

For example in the case of a 10 cm long cavity and biological samples arranged on blocks of 100 micrometers, the size of the mirrors can for example be 1 mm.

Figure 3B:
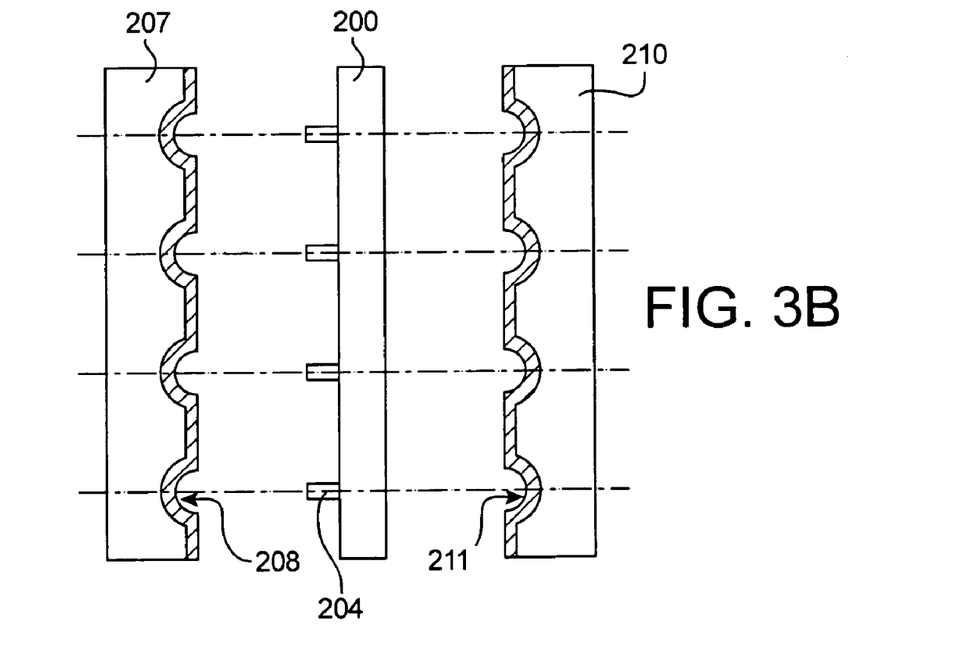

FIG. 3B illustrates another example of a multi-cavity system different from that previously described. It consists of a first matrix 207 of concave mirrors 208 and a second matrix 210 of concave mirrors, the two matrices being opposite and parallel to each other.

Each mirror 208 of the first matrix 207 has a main axis in common with a mirror 211 of the second matrix 210. Each mirror of the first matrix 207 associated with a mirror 211 of the second matrix 210 forms a cavity resonator with an optical axis Δ (represented by dotted lines) on which samples of a biochip 200 can be centred.

Figure 3C:
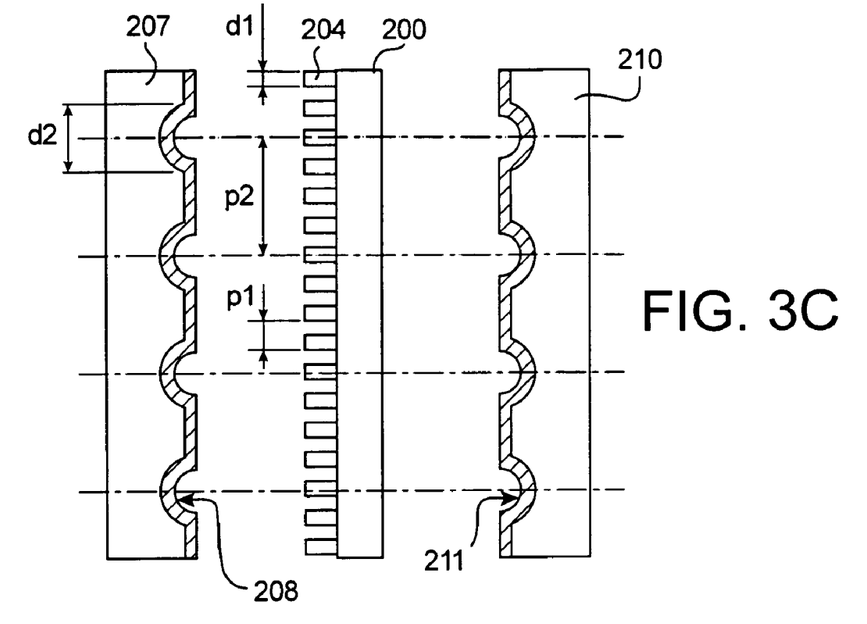

With a multi-cavity system, for example that previously described, where the samples are arranged on a set of blocks 204 with a diameter of $d_1$ and spaced by a step $p_1$ lower than or even much lower than the diameter $d_2$ of mirrors 208 and at one step $P_2$ from the matrix 207 of mirrors 208, there may be a problem of insufficient spatial resolution (see FIG. 3C). Only some of the blocks 204 are placed on the optical axis of a cavity and not all the samples can be measured.

To resolve this problem the support 200 can be shifted along a plane perpendicular to the optical axes of the cavities of the multi-cavity system (the movement being indicated on FIG. 3C by arrows), to enable to place in turn each sample on an optical axis Δ of one of the cavities of the multi-cavity system.

Means enabling to move or shift the support 200 of the samples can be provided. These means can include for example a step-by-step motor with translation plates.

According to a variant, the samples can be integrated or attached directly to one of the reflector means of the multi-cavity system, without relying on a support.

Figure 3D:
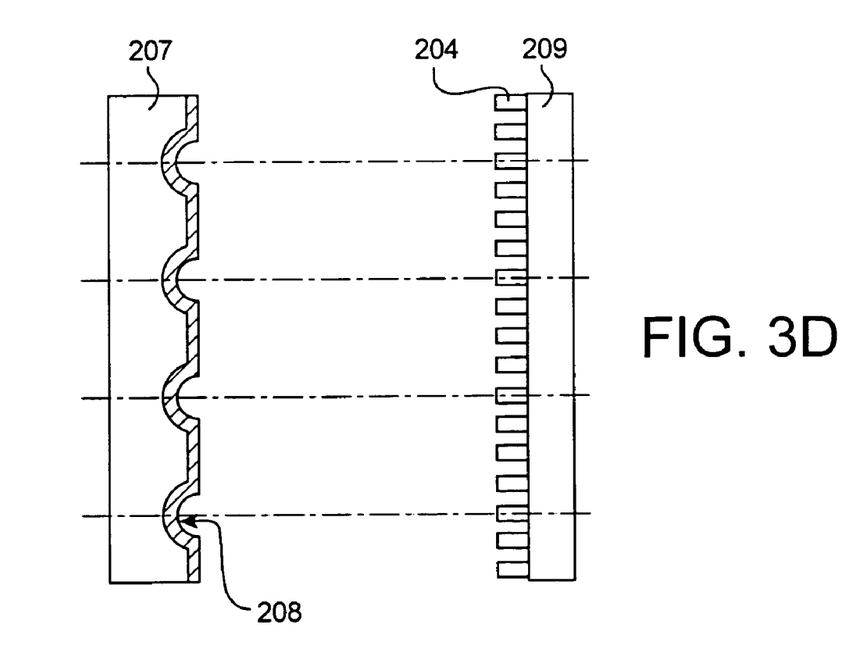

A first example of setting up such a variant is illustrated in FIG. 3D. In this example, the samples to be measured are grafted on blocks 204 integrated in a plane mirror 209. The blocks are arranged on the reflecting surface of the plane mirror 209. The plane mirror 209 is placed opposite a matrix 207 of concave mirrors 208 so as to form a multi-cavity system.

Figure 3E:
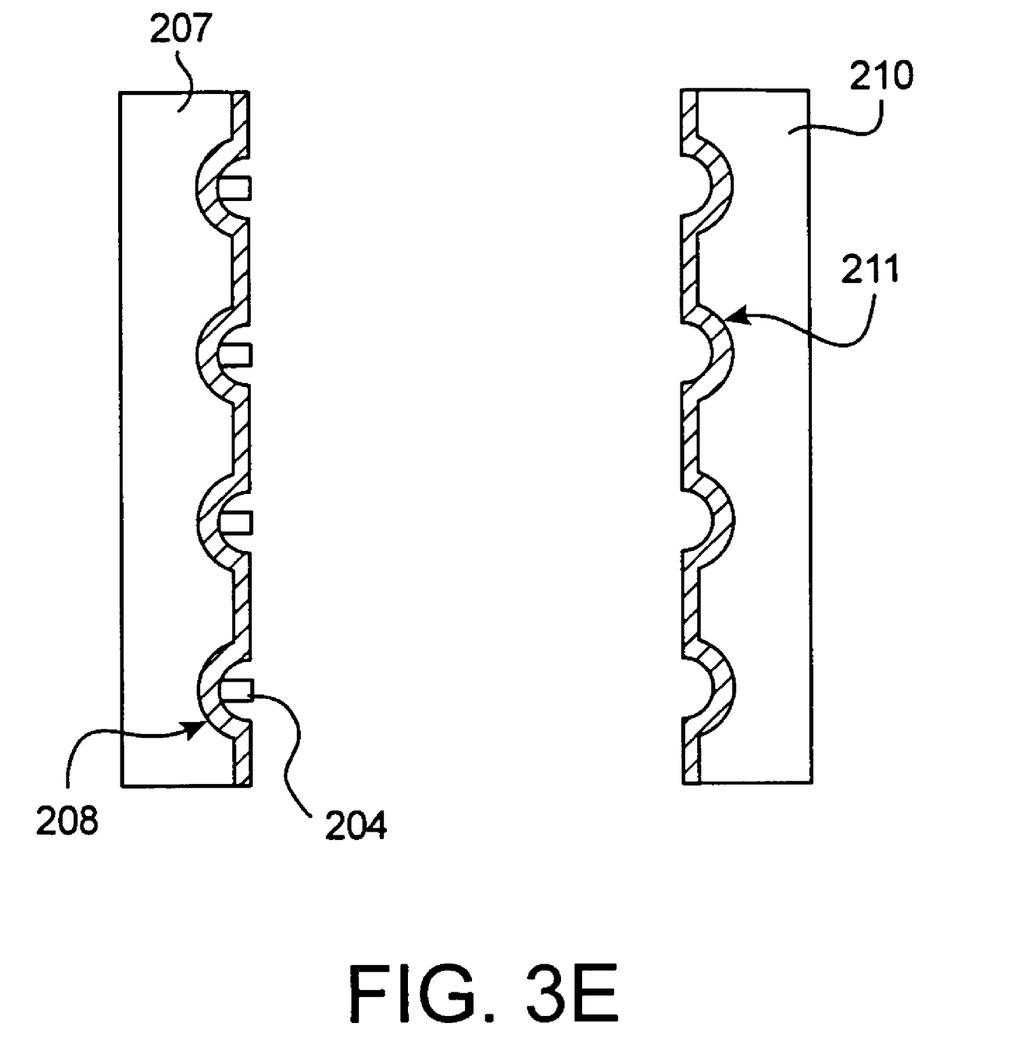

A second example of implementing such a variant is illustrated in FIG. 3E. In this example, the samples are placed on blocks 204 integrated with a matrix 207 of concave mirrors 208. The blocks 204 are arranged on the reflecting surface of the concave mirrors. To form a multi-cavity system the matrix 207 is placed opposite another matrix 210 of concave mirrors 211.

The device implemented according to the invention is not limited to the use of matrices of concave mirrors to form the multi-cavity system. The latter can be obtained for example using matrices of plane mirrors. However, adjusting such a system can turn out to be more delicate than with matrices of concaves mirrors.

Figure 4A:
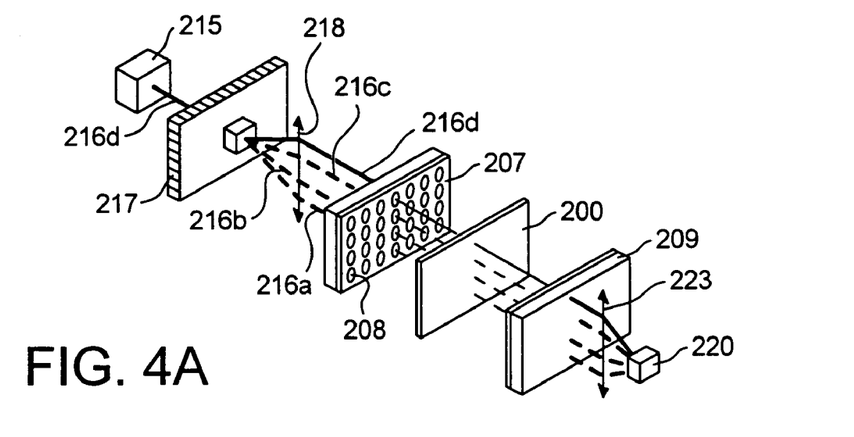
FIGS. 4A, 4B, 4C, illustrate examples of implementing methods according to the invention.

In measuring absorption using a multi-cavity system there is also the problem of being able to address light impulses at a high rate to any target cavity of the system. A light emitting device able to carry out this task is provided as part of the invention and is illustrated in FIG. 4A.

This emitting device can include for example a pulsed laser 215, emitting power between a few dozen kilowatts and a few hundred kilowatts, for example 166 kW, associated with means 217 enabling to deflect impulses emitted by the laser 215 to be deflected.

These deflection means 217 enable light impulses 216a, 216b, 216c, 216d to be sent consecutively and very rapidly to several different cavities of a multi-cavity system formed for example by a matrix 207 of micro-mirrors 208 and a plane mirror 209. The deflection means 217 can take the form of acoustic-optical components functioning in a Bragg operating condition. These components enable to deflect the impulses emitted by the laser 215 in a horizontal and vertical direction respectively.

Each of the acoustic-optical components can be controlled by a low frequency generator enabling the intensity of the light impulses to be modulated using radio frequency waves of variable amplitudes. The frequency of these waves enables to control the deflection of the light beams.

Other deflection methods can be considered in the form of micro-mirrors for example. However, the deflection methods previously described have the advantage in particular of being stable and simple to set up and to enable rapid measurements to be taken.

To acquire signals coming from the multi-cavity system, a detector 220 like a rapid photodetector, a rapid photodiode for example, can be provided for.

Coupling means 218 in the form of one or more lenses associated with a matrix of lenses entering the multi-cavity system for example, can enable to direct light signals to different cavities of the multi-cavity system.

Other coupling means 223 in the form of one or more associated converging lenses coming from the multi-cavity system for example, enable to direct light signals from different cavities of the multi-cavity system towards the same detector 220.

A variant of the device described above is provided for to be able to make several absorption measurements simultaneously on several different samples.

Figure 4B:
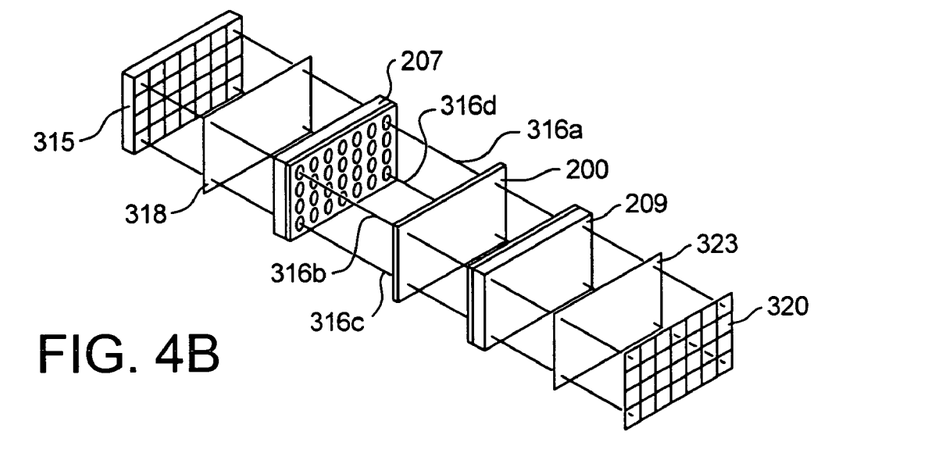

In this variant the detector 220 coming from the multi-cavity system is replaced by several detectors arranged according to a matrix of detectors 320 for example a matrix of photodiodes.

This matrix of detectors 320 can enable several measurements to be acquired in parallel and to obtain an image of the absorption measurements of support samples.

To make these measurement in parallel, several light impulses 316a, 316b, 316c, 316d can be sent simultaneously, each for a sample located in a target cavity of the multi-cavity system.

To emit several light impulses simultaneously towards the multi-cavity system, a matrix of laser sources 315 can be used instead of a single laser.

Coupling means can be provided in order to connect the lasers of the matrix to the multi-cavity system. These coupling means take for example the form of a matrix of lenses 318. Other coupling means can be provided to connect the multi-cavity system with the matrix of detectors 320. These other coupling means take for example the form of another matrix of lenses 323 (FIG. 4B).

Figure 4C:
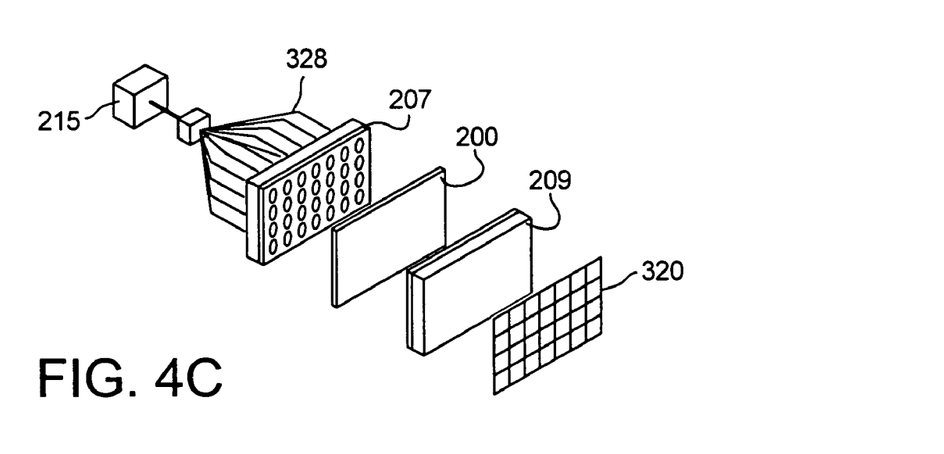

According to a variant, to emit several light impulses simultaneously towards the multi-cavity system one can for example use a laser 215 associated to coupling means different from those previously described, taking for example the form of several optical fibers 328 making it possible to convey light impulses coming from the laser towards the multi-cavity system.

The invention is not limited to the type of measurement previously described based on the lifecycle of photons in a cavity resonator. Variants of the measurement method can be provided using this cavity resonator while remaining within the embodiment of the invention.

The invention can be applied to very fine measurements and for example enable the hybridization of DNA and RNA strands to be measured. In fact the hybridization of DNA or RNA samples can be quantified by measuring the light absorption of these samples.

To carry out such measurements, the DNA or RNA samples can be for example grafted on blocks of a biochip which is then placed in a multi-cavity system. A measurement method can then be applied like those previously described. For example light impulses are sent to a sample in a particular cavity of the multi-cavity system and then the signal coming out of this cavity is measured.

The biochip can for example include a matrix of 50*50 blocks each with a diameter from 1 μm or a few micrometers to 100 μm or a few hundred micrometers for example 300 μm. The number of blocks is not limited. According to another example the biochip can include a matrix of 5000*5000 blocks each with a diameter from 1 μm to 10 μm.

With regard to the cavities of the multi-cavity system they can have a length from 1 cm or a few centimetres and 2 metres or several metres. A cavity set up according to the invention can have for example a length of the order of 10 cm.

It is possible to make a direct measurement of the light absorption of DNA or RNA strands without the latter being marked.

In this case the emitting source(s) used will for example emit in the ultraviolet domain. These sources can include one or more pulsed lasers emitting to a wavelength of around 250 nm.

According to another variant absorption or light diffusion of previously marked DNA or RNA strands can be measured. The markers used can be for example chemical markers like Cy3 type fluorophores.

Absorption and/or light diffusion can also be measured using a marking of samples by particles. When measuring absorption these particles can be gold-based nanospheres for example with a diameter between 1 nm and 10 nm. When measuring diffusion, bigger nanospheres, for example gold-based and with a diameter between 20 nm and 100 nm or several hundred nanometres can be used.

When Cy3 type fluorophores are exposed under a strong light flow or a continuous light flow they can tend to whiten. When this phenomenon, which can be called <<photo-whitening>> appears the samples then absorb practically no light and any measurement of light absorption becomes highly imprecise.

The measurement method according to the invention has the advantage of being able to display the samples under light rays of very short duration for example of the order of a hundred nanoseconds for a cavity 10 cm long and mirrors with reflectivity ratios of 99.8%. With the measurement method according to the invention, when measuring DNA or RNA strands marked by fluorophores, these strands do not or only slightly suffer the phenomenon of <<photo-whitening>>.

When marked strands are being measured the emitting source of light impulses will emit for example in the visible or infrared domain and can take the form of one or more pulsed lasers, for example YAG type lasers, possibly doubled and emitting at a wavelength of the order of 532 nm or He—Ne type lasers, emitting at a wavelength of the order of 541 nm.

In a variant of the method according to the invention illustrated in FIG. 3D and previously described, one of the reflector means of the multi-cavity system can serve directly as a support for biological samples whose absorption is to be measured. In the context of measuring the hybridization of the DNA and RNA strands, these strands can be for example grafted onto blocks that are directly integrated or attached to a mirror, for example a Bragg type high reflectivity mirror or on mirrors in a matrix of mirrors.

An example method for fabricating a matrix of concave mirrors with film coating will now be described.

The matrix is formed first of all from a substrate 400 based on material such as for example fused quartz or BK7 type glass.

Figure 6:
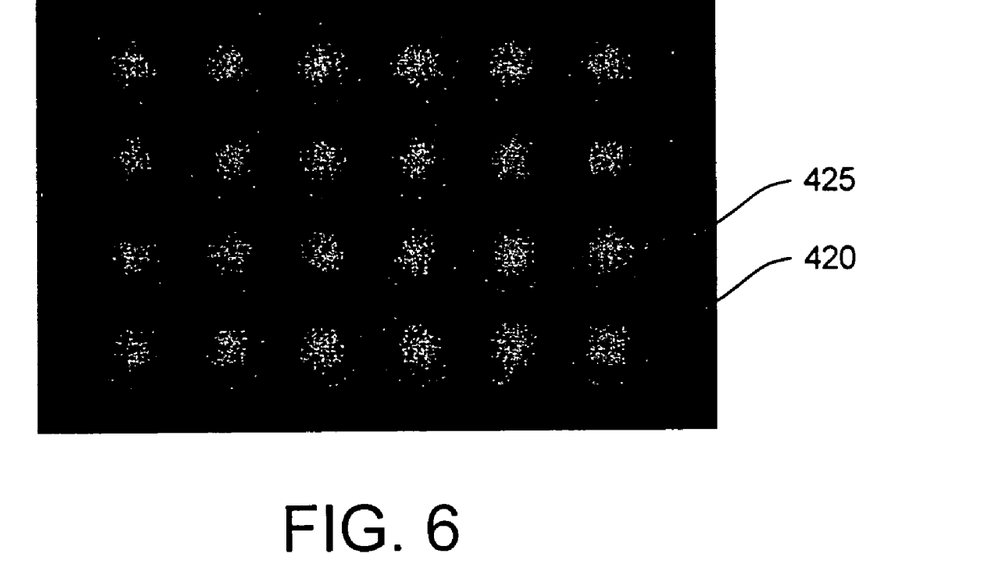

A deposit of a film of photosensitive resin 410 is then made on the substrate for example by a <<spin-coating>> method. The photosensitive resin film 410 is then insulated under a source of incoherent ultraviolet rays through a variable transmission mask like the one illustrated in FIG. 6 for example. This mask has opaque parts 420 with ultraviolet rays and round patterns 425 arranged according to a matrix. These patterns 425 are reproductions of mirror patterns to be formed in a substrate. The patterns 425 of the mask have a transparency which varies from the periphery towards the centre.

Figure 5A:
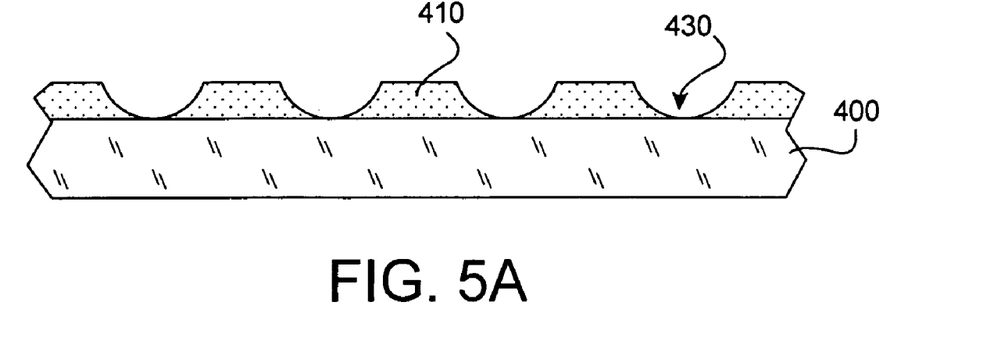
FIGS. 5A-5C, illustrate an example of a method enabling to implement a matrix of mirrors.

The exposition of the resin film 410 through the variable transmission mask makes it possible to modify the physical-chemical properties of the resin according to the illuminance received. By developing the resin with a positive tonality resin, holes 430 in the shape of a hemisphere are obtained (FIG. 5A).

Figure 5B:
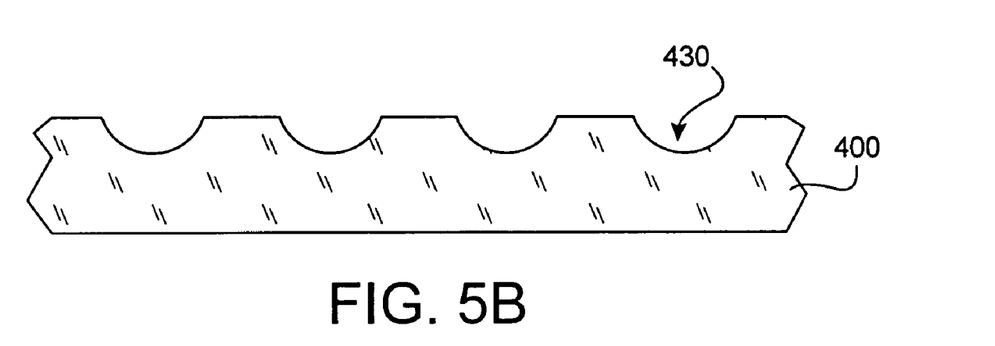
Figure 5C:
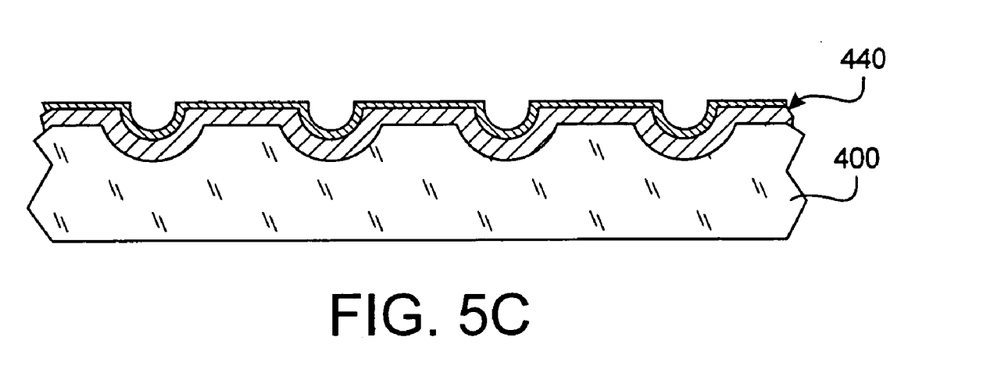

An etching of the substrate 400 is then made through holes 430 so as to reproduce these holes and form a matrix of holes in the substrate 400. These holes can have a diameter of the order of a few micrometers to a few centimetres (FIG. 5B). Then several conformal depositions are made on the engraved substrate so as to form a reflecting multi-layer stack (FIG. 5C).

This multi-layer stack is formed from alternating low refraction index layers based on material like: $SiO_2$, $MgF_2$, $MgF_2$, LiF and high refraction index layers (like: $TiO_2$, $HfO_2$, $Si_3N_4$, $Ta_2O_5$, $Al_2O_3$, $In_2O_3$). This stack enable to make high reflectivity mirrors for example Bragg type. It can be formed with successive deposits like physical deposits in vapour phase (PVD for <<Physical Vapour Deposition>>), or chemical deposit types in vapour phase (CVD for "Chemical Vapour Deposition").

DOCUMENTS CITED

[1]: A. C. Boccara, D. Fournier, J. Badoz: <<Thermo-optical spectroscopy: detection by the "mirage effect">>; Science; November 1979.

[2]: Jiri Homola, Siclair S. Yee, Gunter Gautlitz: <<Surface plasmon resonance sensors>>; Sensor and Actuators 54; 1999.

The invention claimed is:

1. A device for measuring absorption or light diffusion of samples, comprising:
   a first and second reflector device of light rays and in which at least one of the first or second reflector device includes at least two mirrors or a matrix of mirrors integrated within a same support,
   the first and second reflector device configured to form a system of plural cavity resonators.

2. A device according to claim 1, further comprising a light impulse emitting device.

3. A device according to claim 1, further comprising a detection device, enabling to detect light signals coming from the cavity resonator.

4. A device according to claim 1, in which the first reflector device includes a first matrix of concave mirrors, the second reflector device comprising a plane mirror or a second matrix of concave mirrors.

5. A device according to claim 4, further comprising a coupling device between the emitting device and at least one cavity of the multi-cavity system.

6. A device according to claim 4, further comprising a device for deflecting light rays from the light impulse emitting device.

7. A device according to claim 4, further comprising a coupling device to focus light rays from one or more cavities of the multi-cavity system on the detection device.

8. A device according to claim 1, further comprising a support for the samples, placed between the first and second reflector device.

9. A device according to claim 1, in which the samples are based on biological elements, the samples being grafted or integrated on the first or second reflector device.

10. A device for measuring absorption or light diffusion of samples, comprising:
  a first and second light rays reflector device configured to form a system of plural cavity resonators and in which at least one of the first or the second reflector device includes at least two mirrors or a matrix of mirrors integrated within a same support;
  a light impulse emitting device; and
  a detection device, enabling light signals coming from the cavity resonator to be detected.

11. A device according to claim 10, in which the first reflector device includes a first matrix of concave mirrors, the second reflector device comprising a plane mirror or a second matrix of concave mirrors.

12. A device according to claim 10, further comprising a support for the samples, placed between the first and second reflector device.

13. A device according to claim 10, in which the samples are based on biological elements, the samples being grafted or integrated on the first or second reflector device.

14. A device for measuring absorption or light diffusion of samples, comprising:
  a first reflector device including a first matrix of concave mirrors;
  a second reflector device including a plane mirror or a second matrix of concave mirrors, the first and second reflector device configured to form a system of plural cavity resonators; and
  a support for the samples, placed between the first and second reflector devices.

15. A device for measuring light absorption or light diffusion of samples based on biological elements, comprising:
  a first reflector device including a first matrix of concave mirrors;
  a second reflector device including a plane mirror or a second matrix of concave mirrors in which the samples are grafted or integrated into the first or second reflector device,
  the first and second reflector device configured to form a system of plural cavity resonators.

16. A method for measuring absorption or light diffusion of a biological sample, comprising:
  a) placing at least a target sample in at least one cavity resonator or in at least one cavity resonator of a system of plural cavities formed by a first and second reflector device of light rays, at least one of the first or second reflector device including a matrix of at least two mirrors integrated within a same support;
  b) emitting at least one light impulse in the cavity; and
  c) measuring at least a light response signal from the cavity in response to the light impulse, the measurement of the light signal enabling light absorption of the sample to be determined.

17. A method according to claim 16, each light impulse being emitted using one or more pulsed lasers.

18. A method according to claim 16, each response signal being measured at the c) measuring using one or more photodiodes.

19. A method according to claim 16, in which the first reflector device includes a first matrix of concave mirrors, and the second reflector device includes a plane mirror or a second matrix of concave mirrors.

20. A method according to claim 16, each sample being arranged on a support or biochip placed in the cavity resonator.

21. A method according to claim 16, each sample being shifted in the cavity resonator.

22. A method according to claim 16, in which the cavity or multi-cavity system is formed by a first and second reflector device, each sample being grafted or integrated to the first or second reflector device.

23. A method according to claim 16, the biological sample including DNA or RNA.

24. A method for measuring absorption or light diffusion of a biological sample, comprising:
  a) placing at least two target samples among the biological sample, each one in a target cavity of a multi-cavity system formed by a first reflector device and a second reflector device of light rays, at least one of the first or second reflector device including a matrix of at least two mirrors integrated within a same support;
  b) emitting at least one light impulse in each of the target cavities; and
  c) measuring at least two light response signals coming from the target cavities in response to the light impulses, the measurements of the light signals enabling light absorption of the at least two samples to be determined.

25. A method according to claim 24, the light impulses being emitted simultaneously.

26. A method according to claim 24, the response signals being measured simultaneously.

27. A method according to claim 24, each light impulse being emitted using one or more pulsed lasers.

28. A method according to claim 24, each response signal being measured at the c) measuring using one or more photodiodes.

29. A method according to claim 24, in which the first reflector device includes a first matrix of concave mirrors, and the second reflector device includes a plane mirror or a second matrix of concave mirrors.

30. A method according to claim 24, each sample being arranged on a support or biochip placed in the cavity resonator.

31. A method according to claim 24, each sample being shifted in the cavity resonator.

32. A method according to claim 24, in which the cavity or multi-cavity system is formed by a first and second reflector device, each sample being grafted or integrated to the first or second reflector device.

33. A method according to claim 24, the biological sample including DNA or RNA.

34. A method for measuring absorption or light diffusion of a biological sample, comprising:
  a) placing at least two target samples among the biological sample, each in a target cavity of the multi-cavity system formed by a first reflector device and a second reflector device, at least one of the first reflector device or second reflector device including a matrix of at least two mirrors integrated within a same support;
  b) emitting at least one light impulse in each of the target cavities simultaneously; and
  c) simultaneously measuring at least two light response signals coming from the target cavities in response to the light impulses, the measurement of the light signals enabling the light absorption of the at least two samples to be determined.

* * * * *